United States Patent
Kobayashi

[11] Patent Number: 5,825,843
[45] Date of Patent: Oct. 20, 1998

[54] MEDICAL INSPECTION SYSTEM AND METHOD FOR LOCATING POSITION OF PATIENT'S TABLE

[75] Inventor: Shigeo Kobayashi, Chiba, Japan

[73] Assignee: Sony Corporation, Japan

[21] Appl. No.: 638,850

[22] Filed: Apr. 29, 1996

Related U.S. Application Data

[63] Continuation of Ser. No. 299,259, Sep. 1, 1994, abandoned.

[30] Foreign Application Priority Data

Sep. 2, 1993 [JP] Japan .................................. 5-242027

[51] Int. Cl.⁶ ...................................................... A61B 6/04
[52] U.S. Cl. ............................................. 378/20; 378/209
[58] Field of Search ............................. 378/20, 4, 8, 95, 378/205, 206, 208, 209; 250/363.02, 363.05, 363.08

[56] References Cited

U.S. PATENT DOCUMENTS

| | | | |
|---|---|---|---|
| 3,720,817 | 3/1973 | Dinwiddie | 235/151.11 |
| 3,908,126 | 9/1975 | Hudson et al. | 250/320 |
| 4,158,776 | 6/1979 | Barrett | 378/20 |
| 4,613,122 | 9/1986 | Manabe | 378/20 X |
| 5,177,778 | 1/1993 | Tsurumaki | 378/117 |
| 5,204,629 | 4/1993 | Ueyama | 324/318 |
| 5,273,043 | 12/1993 | Ruike | 378/209 X |
| 5,402,462 | 3/1995 | Nobuta | 378/20 |
| 5,411,026 | 5/1995 | Carol | 128/660.03 |
| 5,485,502 | 1/1996 | Hinton et al. | 378/117 |

FOREIGN PATENT DOCUMENTS

0087198A3 8/1983 European Pat. Off. .
A 62-152640 7/1987 Japan .

Primary Examiner—David P. Porta
Attorney, Agent, or Firm—Ronald P. Kananen

[57] ABSTRACT

A medical inspection system comprising a medical inspection part, a patient table movable relative to the medical inspection part and a position detector for locating the position of the patient table. According to the present invention, the system is controlled by various kinds of control computers so that the position of the patient table with respect to the medical inspection can be securely located. This system is applied to a X-ray CT system. The present invention also provides a method for locating the patient table with respect to the medical inspection part of the system.

15 Claims, 6 Drawing Sheets

MEDICAL INSPECTION SYSTEM AND METHOD FOR LOCATING POSITION OF PATIENT'S TABLE

This application is a continuation of application Ser. No. 08/299,259 filed Sep. 1, 1994, now abandoned.

BACKGROUND OF THE INVENTION 1. (Field of the Invention)

The present invention relates to a medical inspection system such as an X-ray CT system and to a method for locating the position of a patient table of the system.

2. (Prior Art)

In the case of the conventional X-ray CT system, the patient is placed on the roof panel of a patient table. Where the roof panel of the patient table is positioned, the relative position between the scanner gantry of the X-ray CT system and the roof panel of the patient table is made use of. This is because where an X-ray CT diagnosis is made, it is necessary for the diagnostician to know the distance from the position at which he desires to start photographing to the affected part of the patient's body. That is, for photographing an X-ray CT image, a fluoroscopic image (scanogram) is used for positioning. In this case, when the target is the patient's head, the photographing position is determined at the same pitch, i.e., 5 mm or 10 mm from the eyeball toward the neck.

In this case, the value for each photographing position itself is not significant. Such a position is a piece of information by which the X-ray CT system manages (i.e., it is used to decide ranking when the CT system displays images). The above-described procedures have been taken for the conventional roentgenography and the diagnostic method based thereon. In the conventional X-ray photography, no positional information has been incorporated in the photographing procedures and it is the present state of the art that the distance from a reference portion of the patient's body (i.e., an internal organ, a bone and etc.) is measured. This fact shows that no coordinate system is required for X-ray photographing.

Further, from the fact that an X-ray photographing system photographs X-ray CT images a plurality of times at certain intervals of time, the introduction of the concept of "absolute position" follows as a logical consequence so that it becomes necessary to set the patient's body at a certain position at all times.

This is impractical when we consider that the patient is a human being and his health condition is always changing with time. Even a healthy person can not reproduce the same posture and position at an interval of time.

For the above reasons, it has conventionally been practiced without exception that a fluoroscopic image is photographed and after positioning, a CT image is photographed.

Accordingly, in the conventional X-ray CT system, the position of the roof panel of the patient table is not measured on the basis of the absolute position.

FIG. 5 shows the routine of a method for positioning the roof panel of the patient table in the above-described conventional X-ray system. In FIG. 5, photographing position data for CT image photography can be set as desired. As an example, the patient's head P is shown in an image (scanogram) G displayed on a monitor by CT scan photography and a slice initiating position IP is set with a positioning cursor C.

Next, the roof panel R of the patient table T is automatically moved to the slice initiating position IP. In the example shown in FIG. 5, the central portion of the patient's head P is set to the slice initiating position IP. In the example shown in FIG. 5, the central portion of the patient's head P is set to the slice initiating position IP. In a coordinate system with the slice initiating position IP being 0 mm, the direction in which the roof panel R of the patient table T enters the scanner gantry is set to a minus (−) direction and the direction opposite thereto is set to be a plus (+) direction. Then CT scan photography is initiated.

Usually, the same person is subjected to photographing again at a certain time interval (at least one day) from his first photographing but the positional relationship between CT images obtained in different time zones is not regarded as a matter of so much importance. Further, in the case of the patient table of any of the existing CT systems, the roof panel and the body of the patient table are connected by a mechanical latch mechanism. Therefore, as an emergency measure, only the roof panel can be made manually movable by releasing the mechanical latch mechanism by hand. Therefore, it has hitherto been considered that it is not necessary for the diagnostician to know the absolute position of the patient table.

From the foregoing, the existing X-ray CT systems employ neither hardware nor software measures for relating the position of the patient table to that of the scanner gantry. In other words, the diagnostician or operator can not accurately locate the position of the roof panel of the patient table with respect to the position of the scanner gantry at all times. By the way, it should be noted that the vertical position of the patient table is measured with a potentiometer or other similar measuring means and the height of the patient table is controlled on the basis of the absolute (or reference) position. Consequently, the existing X-ray CT systems are accompanied with the following problems.

That is, referring to FIG. 6, when the patient table T is lowered in the direction F with the roof panel R delivered into the scanner gantry S, the roof panel R and the scanner gantry S interfere with each other. The reason for this is that even when the projecting portion of the roof panel R lies in the opening OP of the scanner gantry S, it can not be detected because there is no device for identifying the positional relationship between the roof panel R and the scanner gantry S and hence the interference therebetween can not be avoided.

In addition, of the conventional CT systems, there is, as shown in FIG. 7, one that has such an interlocking means as inhibiting the delivery of the roof panel R when the position of the patient table T is lower than the lowest position of the opening OP of the scanner gantry S. However, when its mechanical latch mechanism is released, the roof panel R can be moved manually. In this manual operation, both the roof panel R and the scanner gantry S interfere with each other, still.

The above interlock is a device that prevents, through a control circuit, the occurrence of an abnormal operation in response to a certain operation, thereby preventing the occurrence of a danger or that abnormal operation, or a device for inhibiting the initiation or continuation of the operation of the equipment unless preset conditions are satisfied.

Further, as shown in FIG. 8, the scanner gantry S has a mechanism which causes the scanner gantry itself to tilt in the direction of the arrow E and an interlock for controlling the amount of tilting of the scanner gantry S depending on the vertical position of the patient table T is employed. Further, for the scanner gantry S which has already been tilted, the operation of lifting the patient table T in the direction of the arrow G is controlled by an interlock.

However, if the patient table T is further lowered in the direction of the arrow F or the scanner gantry S is further tilted in the state shown in FIG. 8, the roof panel R and the scanner gantry S may interfere with each other at a point PO of the opening OP of the scanner gantry S. This is because the positional relationship between the scanner gantry S and the patient table T can not be identified.

Further, in the conventional X-ray CT system, offset measuring processing known as air calibration is executed to measure an offset quantity of a detector at the time of termination of the warming-up immediately after the starting of the system and during the use (every 2 or 3 hours). This offset measurement is one of the important processings because an offset has a great effect on the quality of CT images.

During the air calibration, the opening of the scanner gantry must be kept empty. If this air calibration is performed in a state in which the roof panel or the like is within a X-ray photographing region, the offset quantity becomes faulty resulting in deteriorating the CT scan image quality.

In the conventional X-ray CT system, the position of the roof panel is not controlled on the basis of the absolute position as described above, it is impossible to recognize whether or not the roof panel lies in the X-ray photographing region when air calibration is started. Therefore, the diagnostician or operator moves the roof panel sufficiently away from the X-ray photographing region in advance of the initiation of air calibration.

Some X-ray CT systems are arranged to display on a monitor or the like a message for prompting the diagnostician or operator to move the roof panel at the time of initiating air calibration. However, there has hitherto been no system that can automatically identify the position of the roof panel for checking purposes (because the roof panel position is not controlled on the basis of the absolute position. Consequently, even if air calibration is performed with the roof panel lying in the X-ray photographing region, the diagnostician or operator may not become aware of the failure of air calibration until he obtains CT images because the system has no function of checking whether or not the roof panel is present in the X-ray photographing region. This also leads to the lowering of operating efficiency.

SUMMARY OF THE INVENTION

Accordingly, an object of the present invention is to provide a medical inspection system which is capable of securely locating the position of a patient table forming part thereof.

Another object of the present invention is to provide a method of securely locating the position of the patient table of the medical inspection system.

To attain the above objects, the medical inspection system according to the present invention comprises a medical inspection portion for making a medical inspection of a patient, a patient table for delivering the patient placed thereon to the medical inspection portion, and a position detecting device for locating the position of the patient table moving toward the medical inspection portion. In the present invention, the medical inspection system is preferably an X-ray CT system. Further, the position detecting device is preferably disposed between the medical inspection part and the patient table and is preferably adapted to locate the position of the patient table by transmitting an ultrasonic wave.

Further, the method of locating the position of the patient table is performed such that the movement of the patient table relative to the medical inspection portion for making a medical inspection of a patient is detected. The position of the patient table is preferably located by a height detector using an ultrasonic wave and the medical inspection portion is preferably a scanner gantry of an X-ray CT system.

In the above-described arrangement, the position detecting device detects the movement of the patient table toward the medical inspection portion to thereby prevent interference between the medical inspection portion and the patient table.

Further, where the present invention is applied to an X-ray CT system, for example, whether or not a part of the patient table lies in the medical inspection portion is detected by the position detecting device when air calibration is carried out.

PREFERRED EMBODIMENTS OF THE INVENTION

Preferred embodiments of the present invention will now be described in detail with reference to the accompanying drawings.

It should be noted in this connection that the following embodiments are preferred specific examples of the present invention so that various technically preferable limitations are imposed but the scope of the present invention is not limited to these embodiments unless otherwise specified in the following description.

Figure 1:
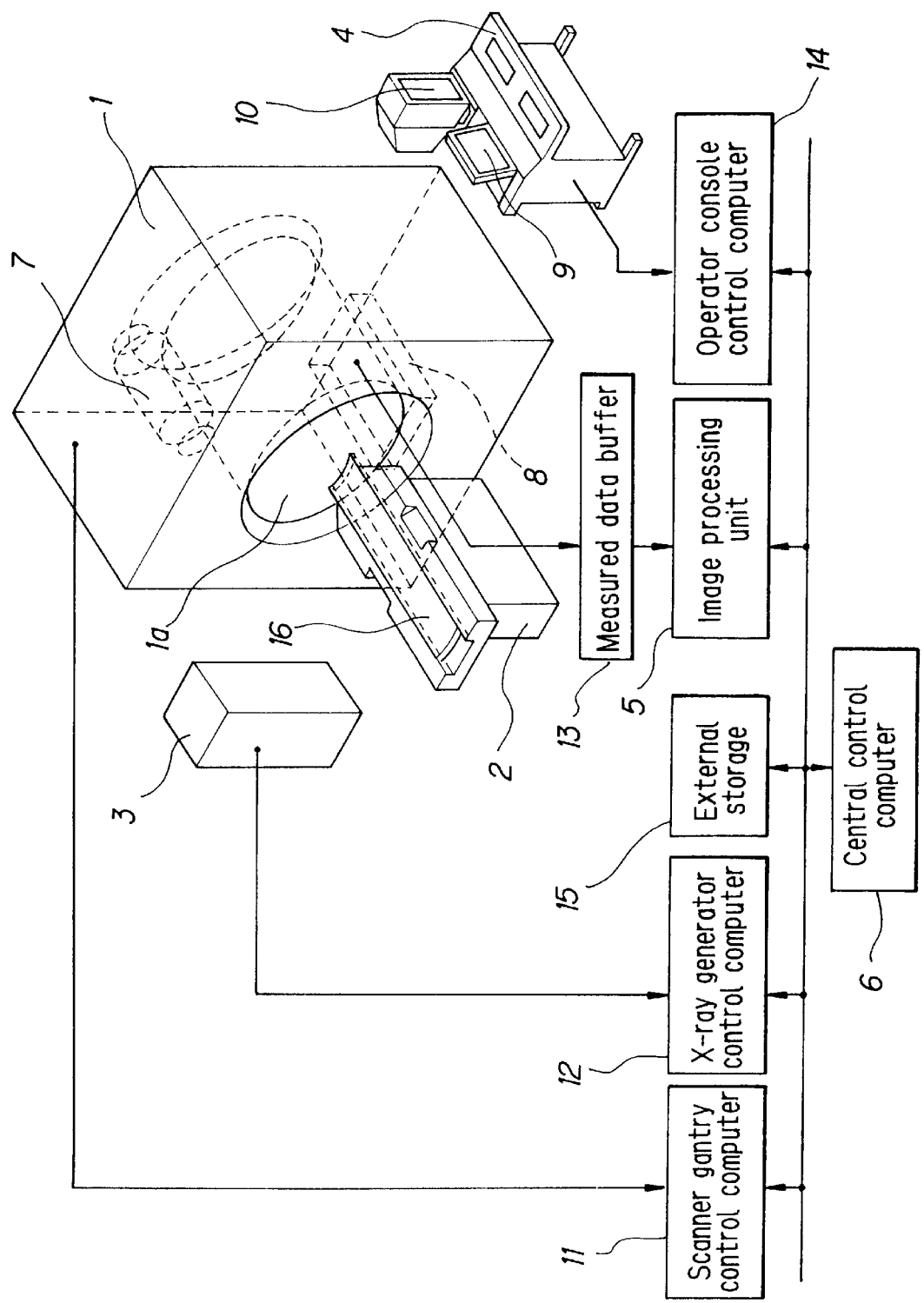
FIG. 1 is a block diagram of an X-ray CT system as a preferred embodiment of a medical inspection system according to the present invention.

Now, referring to FIG. 1 which is a block diagram of a X-ray CT system as a preferred embodiment of a medical inspection system according to the present invention, the X-ray CT system roughly comprises a scanner gantry 1, a patient table 2, a X-ray control unit 3, an operator console 4, an image processing unit 5 and a central control computer 6. The scanner gantry 1 forms itself a medical inspection part. Further, the scanner gantry 1, the X-ray control unit 3 and the operator console 4 are provided with control computers 11, 12 and 13, respectively.

The scanner gantry control computer 11 controls mechanisms included in the scanner gantry 1 and also controls the horizontal and vertical movements of the patient table 2. Further, the scanner gantry control computer 11 monitors the input condition of an operation panel (not shown) installed on the surface of the scanner gantry 1 and displays information on the position and height of a roof panel 16 of the patient table 2.

The X-ray generator control computer 12 controls a generated X-ray output and monitors whether or not the X-ray control unit 3 is in its normal state.

The operator console control computer 14 monitors the input condition of switches on the operator console 4, displays information by display devices formed of LEDs and by a segment type display device.

Within the scanner gantry 1 there are disposed on the some rotary plate (not shown) an X-ray tube 7 and an X-ray detector 8 in opposite relationship with each other.

When X-ray CT images are to be photographed, an object of inspection (i.e., a patient) placed on the roof panel 16 of the patient table 2 is moved in advance into an aperture 1a or an opening of the scanner gantry 1 and then the rotary plate having the X-ray tube 7 and the X-ray detector 8 mounted thereon is rotated through 360° around the patient for X-ray radiation thereby collecting data. That is, by rotating the rotary plate, a predetermined portion of the patient's body is subjected to X-ray CT scanning.

Thus, the pieces of data collected from the X-ray detector 8 are sent to a measured data buffer 13 in sequence and after analog-digital signal conversion, CT image data is stored therein. The stored raw data on CT images is then transferred to the image processing unit 5 where a X-ray CT image is formed by reconstructive operation processing.

The X-ray CT image thus formed is displayed on an image display monitor 10 provided on the operator console 4 and also stored in an external storage 15.

An operation monitor 9 is used by the central control computer 6 to display information for guiding and supporting the diagnostician or operator in operation and also display the operating conditions of the system.

Next, the CT image photographing method by the X-ray CT system will be described.

In FIG. 1, the diagnostician or operator keeps the roof panel 16 moved into the aperture 1a of the scanner gantry 1 in advance together with a patient thereon in advance. Then, the diagnostician or operator selects and sets CT image photographing conditions by using the operator console 4 and the operation monitor 9. The photographing conditions vary depending on the portion of the patient's body to be photographed and mainly composed of X-ray generating conditions (tube voltage, tube current, scanning time and etc.) and image reconstructing conditions (number of display matrices, filter configuration, magnifying power and etc.).

Upon determination of photographing conditions, the central control computer 6 reads out them from the operator console control computer 14, changes the format of the photographing conditions to a predetermined one and issues a "photographing preparation" instruction to both the scanner gantry control computer 11 and the X-ray generator control computer 12.

In a system that is attended with the generation of X-rays, the rotor (i.e., a target rotating anode) in the X-ray tube is started and when it has come to rotate at a constant speed, the X-ray generator control computer 12 gives a preparation completion instruction to the central control computer 6.

In the scanning gantry, on the other hand, the X-ray tube 7 and the X-ray detector 8 must remain stationary at a predetermined position (i.e., initial position) at the time of starting CT image photographing.

Accordingly, if the X-ray tube 7 and the X-ray detector 8 are not at the initial position when the "photographing preparation" instruction is issued from the central control computer 6, the scanner gantry control computer 11 detects it and executes a processing for returning the X-ray tube 7 and the X-ray detector 8 to the initial position.

When the preparation is completed in all the units and the control computers 11, 12 and 14 for the units recognize the preparation completion, the central control computer 6 gives an X-ray exposure instruction to the X-ray generator control computer 12 and also instructs the image processing unit 5 to initiate capturing X-ray data.

CT image photographing is effected by rotating both the X-ray tube 7 and the X-ray detector 8 through more than 360° around the patient's body, which has been moved into the aperture 1a of the scanner gantry 1, thereby collecting data. However, some X-ray CT systems are designed so that data collection can be effected by rotating the X-ray tube 7 and the X-ray detector 8 through not more than 300° in order to minimize the exposure to X-rays and reduce the influence of the movement of the patient's body due to breathing, for example.

Data that is obtained by one X-ray exposure (pulse exposure) or one data sampling (continuous exposure) is called 1 view (or 1 projection). During one revolution of the X-ray tube 7 and the X-ray detector 8, a predetermined number of views are obtained.

Since the data outputted by the X-ray detector 8 is in the form of analog signals, they are converted into digital signals and then sequentially stored into the measured data buffer 13.

Simultaneously with the initiation of the X-ray exposure, the central control computer 6 gives the image processing unit 5 an image reconstruction operation initiation instruction. The reason why such instruction is given to the image processing unit 5 simultaneously with the initiation of X-ray exposure is that the system is designed so as to minimize the time interval from the termination of the X-ray exposure to the formation of a CT image. The image processing unit 5 that has been given the instruction sequentially reads out data from the measured data buffer 13 and initiates image reconstruction operation.

Thus, upon formation of a CT image, the image processing unit 5 displays it on the image display monitor 10 and stores the CT image in the external storage 15. Further, if desired, the raw data stored in the measured data buffer 13 is similarly stored in the external storage 15.

Figure 2:
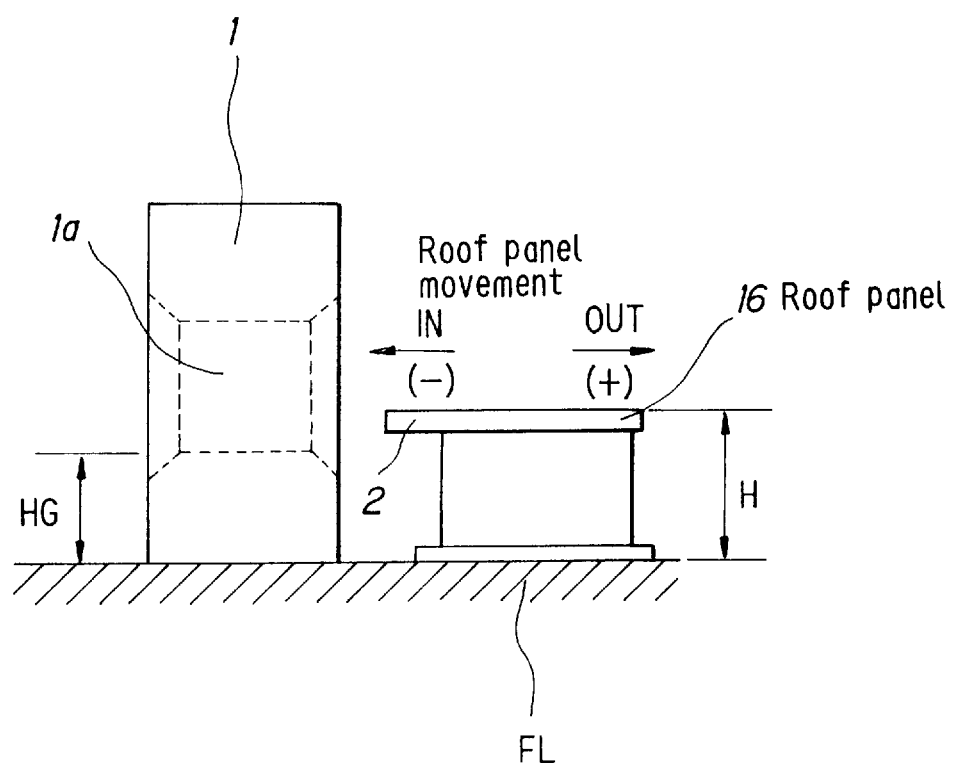
FIG. 2 is a diagram showing a scanner gantry and a patient table included in the X-ray CT system shown in FIG. 1.

Next, referring to FIGS. 2 and 3, the relationship between the scanner gantry 1 and the patient table 2 is as follows:

The roof panel 16, which is also called the top of the patient table, is movable in directions IN and OUT. The IN direction is assumed to be minus (−) direction and the OUT direction sis assumed to be (+) direction. The height of the roof panel 16 from the floor FL is represented by H and the lowermost height of the opening 1a of the scanner gantry 1 is represented by HG.

Figure 3:
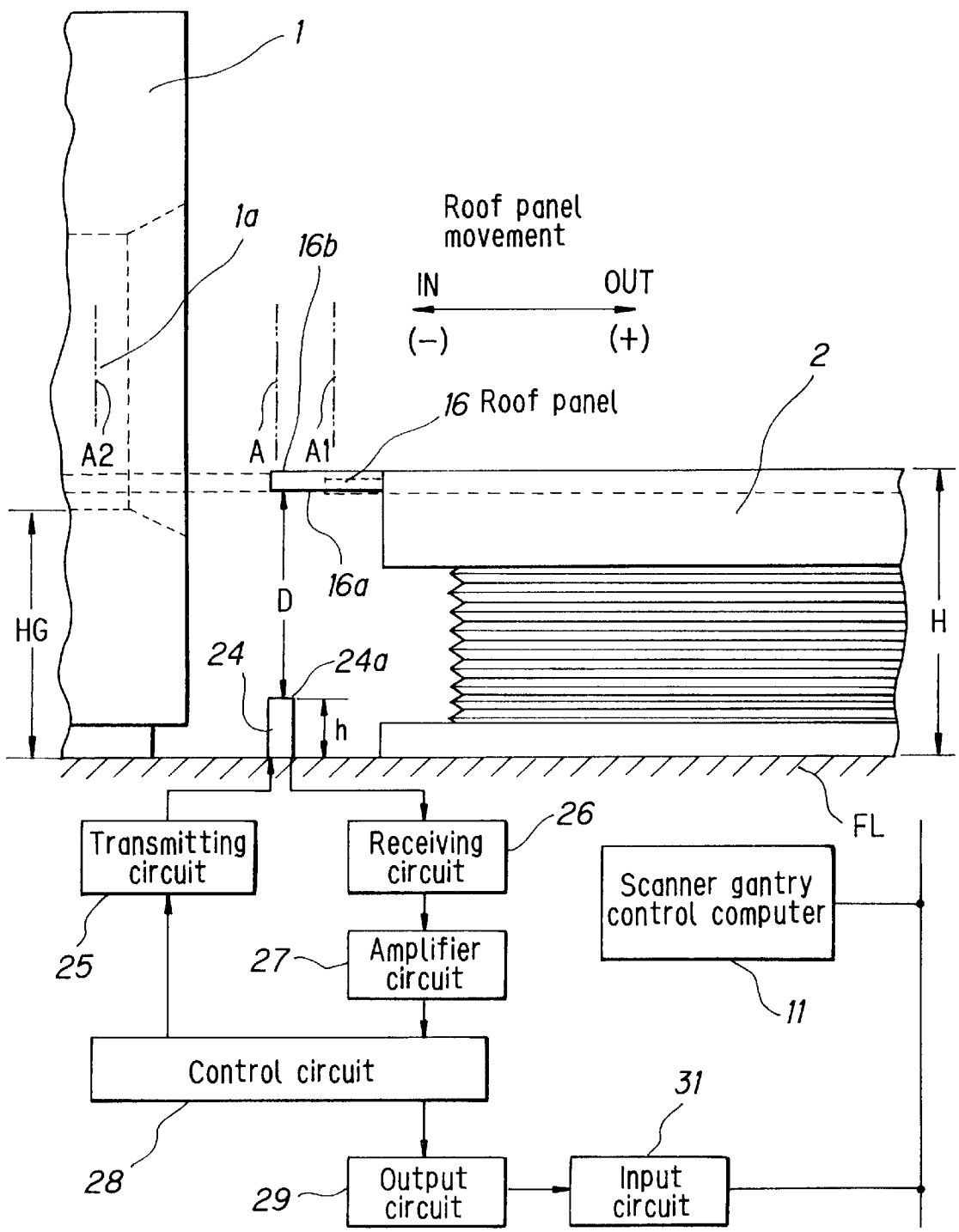
FIG. 3 is a diagram showing in detail relationships among the scanner gantry, the patient table and a detector included in the X-ray CT system shown in FIG. 1.

As shown in FIG. 3, a detector 24 which serves as a position detector for the roof panel 16 is disposed between the scanner gantry 1 and the patient table 2. The detector 24 is preferably disposed on the floor FL to detect whether or not the roof panel 16 has been delivered (projected) toward the scanner gantry 1 by generating an ultrasonic wave. Specific examples which can be employed as the detector 24 include a horn (acoustic synthesizer) accommodated in a shielded casing, a piezoelectric vibrator and an aerial ultrasonic vibrator formed from a damper.

As shown in FIG. 3, the detector 24 is connected to a transmitting circuit 25 and a receiving circuit 26. The transmitting circuit 25 is connected to a control circuit 28 and the reception circuit 26 is connected to the control circuit 28 through an amplifier circuit 27.

The system is arranged such that on the basis of a signal from the transmitting circuit 25, the detector 24 transmits an ultrasonic wave toward the lower surface 16a of the roof panel 16 and the ultrasonic wave reflected from the lower surface 16a of the roof panel 16 can be received by the receiving circuit 26.

The amplifier circuit 27 amplifies an analog signal from the receiving circuit 26. The control circuit 28 is adapted to control the whole circuit and to calculate the distance from the detector 24 to the roof panel 16.

An output circuit 29 is connected to the control circuit 28 to convert a digital signal from the control circuit into a desired output form (from digital to analog signal). The output circuit 29 is also connected to an input circuit 31 which is connected directly to the scanner gantry control computer 11.

Generally, there are two different ultrasonic detector systems of which one is the pulse-echo system in which distance measurement is effected by measuring a time interval from the moment an ultrasonic wave is transmitted from a detector to the moment the ultrasonic wave reflected from an object returns to the detector and the other is the FM-CW (frequency-modulated continuous wave) system in which distance information is sampled by using a frequency-modulated continuous wave. In the present invention, however, either of the ultrasonic detector systems may be used without any restriction.

The position A shown in FIG. 3 is the position of the roof panel 16 which can be detected by the detector 24 whereas the position A1 is the position of the roof panel which can not be detected by the detector 24. Further, the position A2 roughly shows one example of the position of the roof panel 16 during CT image photographing. As long as the distal end 16b of the roof panel 16 is forwardly of at least the position A as viewed in the IN (−) direction, it is possible to detect that the roof panel 16 has been delivered toward the scanner gantry 1. Since the roof panel 16 has been completely delivered into the aperture 1a of the scanner gantry 1 when CT image photographing is carried out, the detector 24 can securely detect the roof panel 16.

Further, in FIG. 3, H designates the height of the roof panel 16 and D designates the distance between the detecting surface 24a of the detector 24 and the lower surface 16a of the roof panel 16. In addition, h designates the height of the detecting surface 24a from the floor FL forming a system installation surface. If the height h is already known, the height H of the roof panel 16 and the distance D can be calculated from the following mathematical expression 1. Assuming that the height (or distance) from the system installation surface FL to the lower end of the scanner gantry aperture 1a is HG, if H≦HG, the roof panel 16 will interfere with (or run against) the scanner gantry 1 during movement of the roof panel 16.

$$H = D + h \tag{1}$$

Next, a method of detecting delivery of the roof panel and a method of obtaining the height of the roof panel according to the present invention will be described.

The transmitting circuit 25 generates an ultrasonic wave through the detector 24. If the roof panel 16 has been delivered toward the scanner gantry 1 to such an extent that the distal end 16b of the roof panel 16 is closer to the aperture 21 of the scanner gantry 1 than the position A, the ultrasonic wave is reflected from the roof panel 16 to return to the detector 24. The returned ultrasonic wave is then received by the receiving circuit 26 which latter generates an analog signal. The analog is then amplified by the amplifier circuit 27 and sent to the control circuit 28.

In the control circuit 28, the distance D between the detecting surface 24a and the roof panel 16 is measured by the either of the two systems described above (particularly the pulse-echo system is the mainstream). The measured data is outputted to the scanner gantry control computer 11 by the output circuit 29.

The scanner gantry control computer 11 recognizes the output data and displays in on a 7-segment display device or the like (not shown) provided on the operator console 4, shown in FIG. 1.

Since the scanner gantry control computer 11, shown in FIG. 3, also controls the horizontal movement and rising and lowering operations of the roof panel 16 of the patient table 2, as described above, it is also possible to decide whether or not to allow horizontal movement of the roof panel 16 on the basis of the data from the output circuit 29.

If the height HG of the aperture 1a of the scanner gantry 1 is not lower than the height H of the roof panel 16, horizontal movement of the roof panel 16 of the patient table 2 is disallowed. Conversely, if the detector 24 has already detected the delivery of the roof panel 16, it is also possible to disallow rising and lowering operations of the patient table 2.

The conventional X-ray CT systems have already been provided with a function of detecting the heightwise position of the patient table always by the absolute position. Generally, this detecting function is realized with a potentiometer, an encoder, etc. The reason for this is to provide an interlock between the height of the patient table 2 and the height of the aperture 1a of the scanner gantry 1.

In contrast, according to the instant embodiment, there are cases where no ultrasonic wave can be received by the detector 24, which is connected to the control circuit 28 shown in FIG. 3. For example, a case where the distal end 16b of the roof panel 16 is at the position A1 in FIG. 3, or a case where the roof panel 16 is at a distance where it cannot be detected from the detector 24. The case where the roof panel 16 is at a distance where it cannot be detected from the detector 24 is a case where the roof panel 16 is at a considerably high position from the floor FL because of the rising operation of the patient table 2.

Therefore, the control circuit 28 shown in FIG. 3 has previously been provided with a function whereby a signal can be outputted from the output circuit 29 only when the roof panel 16 as an object of detection is within a certain distance range, or only when the object of detection is outside a certain range.

Accordingly, it is also possible to arrange the system such that when the distal end 16b of the roof panel 16 is at the position A1, or when the roof panel 16 is at a distance where it cannot be detected from the detector 24, as described above, the output circuit 19 outputs a signal so that the scanner gantry computer 11 recognizes it.

With this method, the scanner gantry control computer 11 can recognize the delivery of the roof panel 16, and it is therefore possible to prevent an interference between the scanner gantry 1 and the roof panel 16 in the same way as the above.

In the conventional X-ray CT systems, the gap between the scanner gantry 1 and the patient table is small, and the scanner gantry 1 is frequently titled during CT image photographing.

It is possible to adopt an interlock whereby when the scanner gantry 1 is titled, the scanner gantry control computer 11 recognizes delivery of the roof panel 16 to prevent an interference between the scanner gantry 1 and the roof panel 16.

In addition, in a case where offset measuring processing (air calibration) is carried out, as described above, when the roof panel 16 lies in the aperture 1a of the scanner gantry 1, the presence of the roof panel 16 can be recognized. In this case, if the presence of the roof panel 16 is recognized, alarm display can be made on the operator console 4, for example, through the central control computer 6 and the operator console control computer 14, which are shown in FIG. 1.

Figure 4:
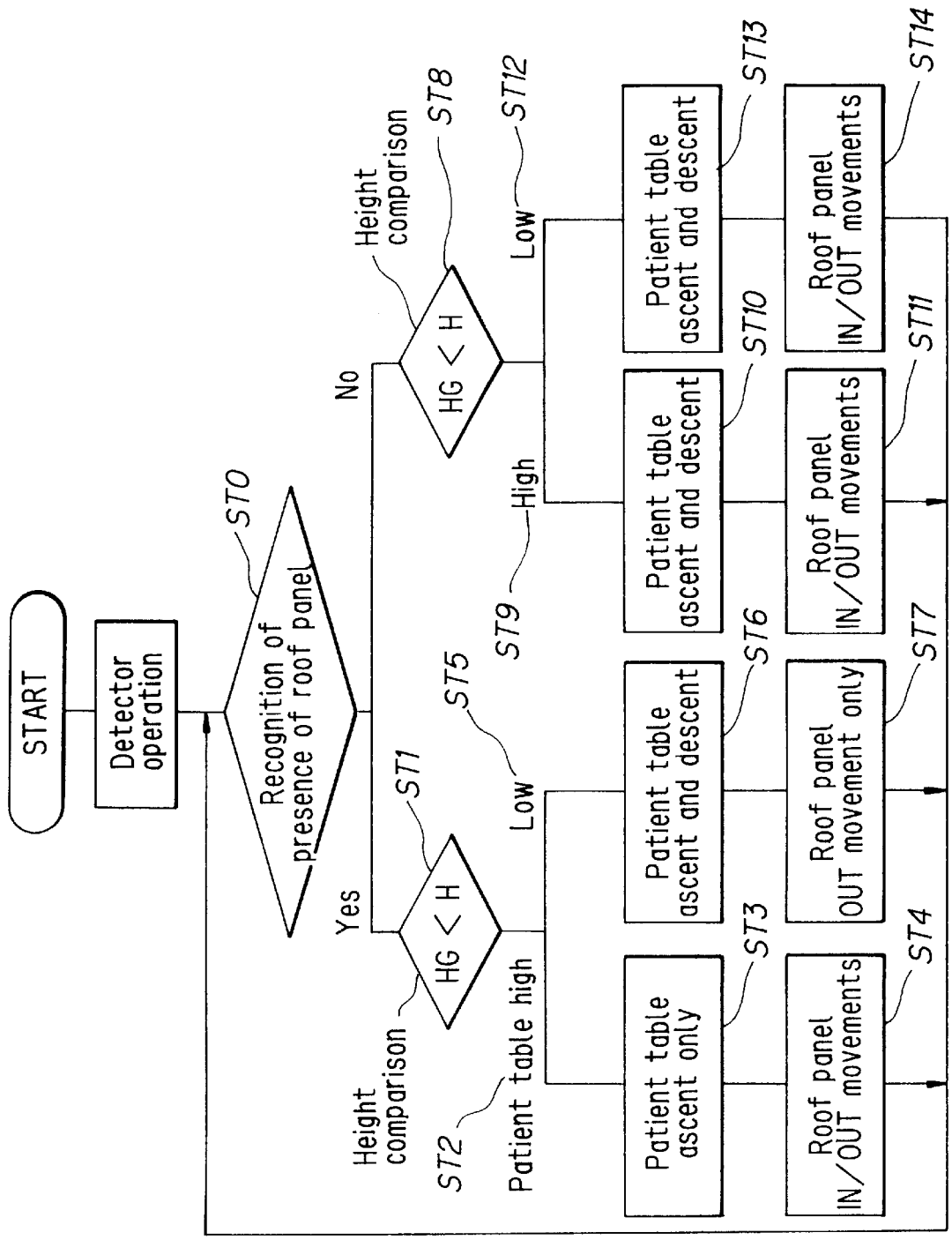
FIG. 4 is an illustration of how the position of the roof panel of the patient table of the X-ray CT system shown in FIG. 1 is located following the delivery of the table.
Figure 5:
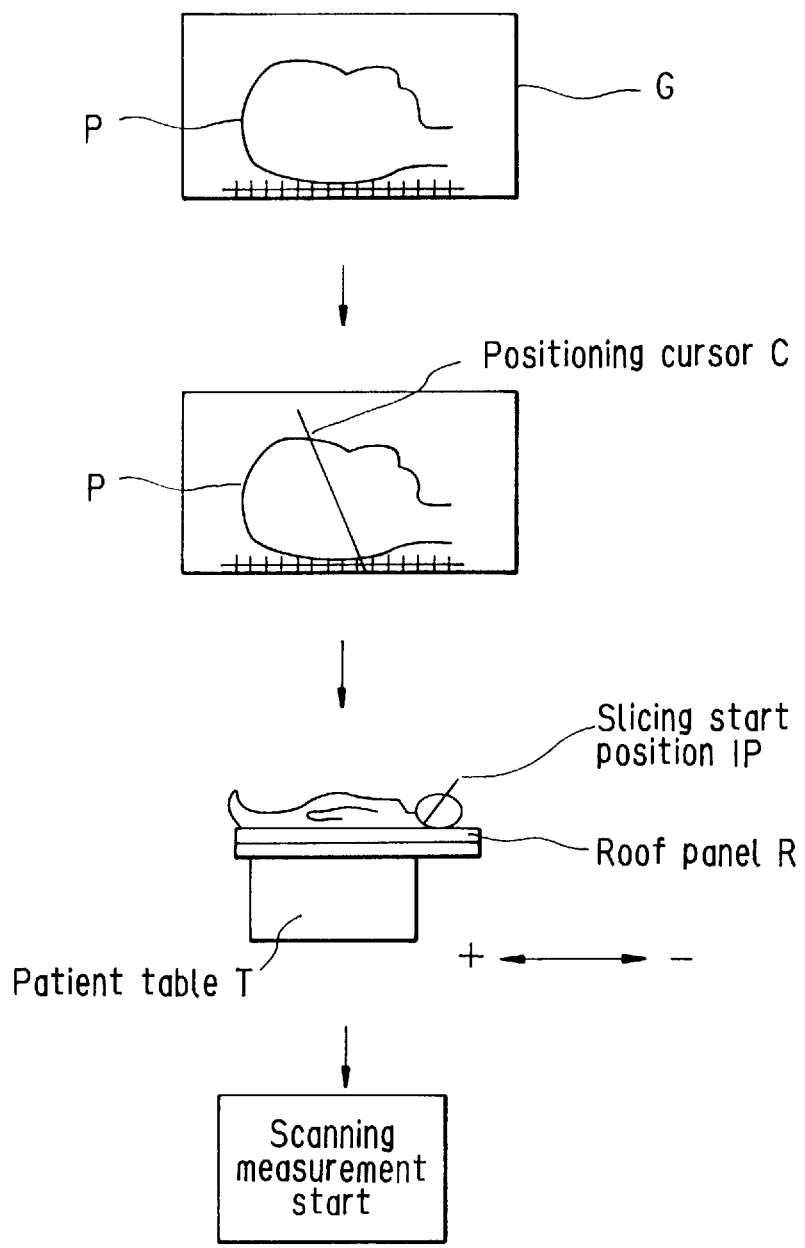
FIG. 5 is an illustration of how a roof panel of a patient table of a conventional X-ray CT system is positioned.
Figure 6:
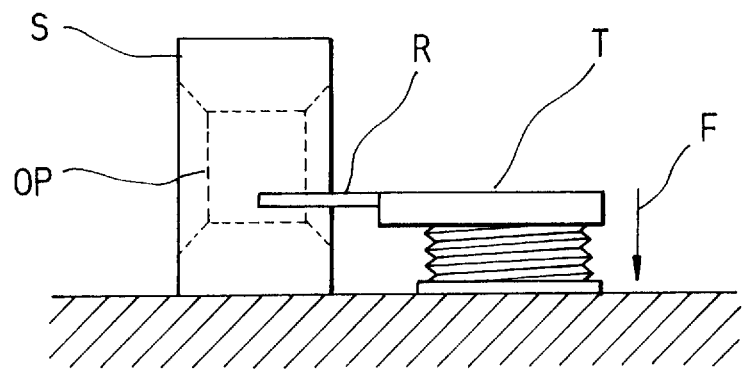
FIG. 6 is a diagram showing the positional relationship between a scanner gantry and the roof panel of the patient table of the conventional X-ray CT system shown in FIG. 5.
Figure 7:
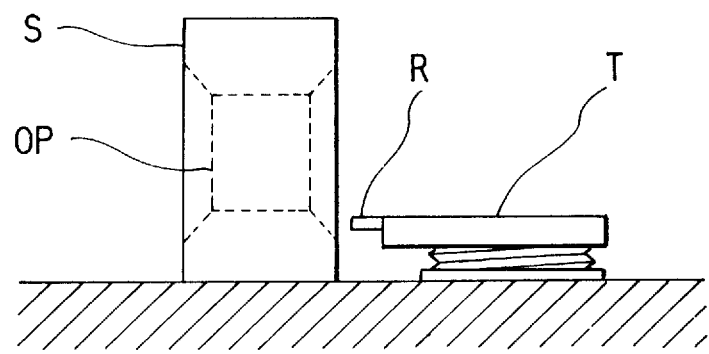
FIG. 7 is a diagram showing the positional relationship between the scanner gantry and the roof panel of the patient table of the conventional X-ray CT system when the vertical position of the roof panel is lower than the height of an opening of the scanner gantry.
Figure 8:
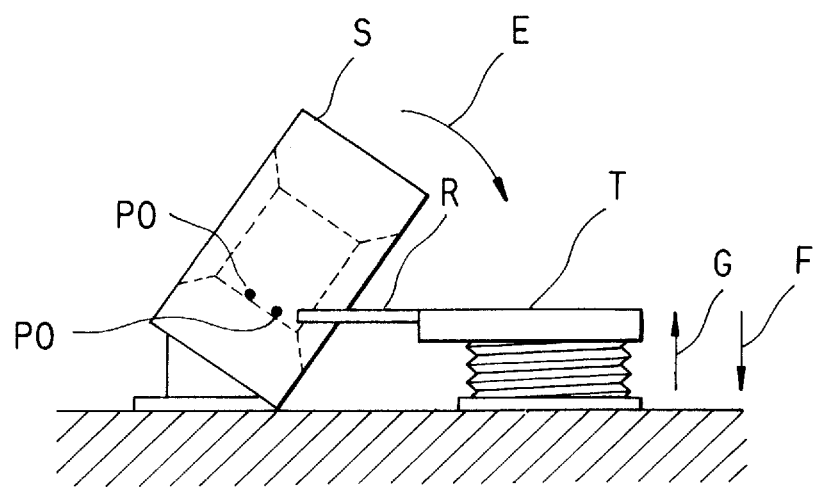
FIG. 8 is a diagram showing an example in which the scanner gantry of the conventional X-ray CT system is tilted during use of the system.

Next, FIG. 4 will be referred to.

FIG. 4 is a sequence flowchart showing an example of use of the X-ray CT system according to the present invention when the diagnostician or the operator manually operates the scanner gantry 1 show in FIG. 1.

The sequence flowchart shown in FIG. 4 mainly describes the procedure in which the scanner gantry control computer 11 shown in FIG. 3 judges whether or not the roof panel 16 has been delivered toward the scanner gantry 1.

The ultrasonic detector 24 shown in FIG. 3 is always in an operative state, and the scanner gantry control computer 11 is in operation to recognize the height H of the patient table 2 and deliver of the roof panel 16.

The scanner gantry control computer 11 limits the vertical movement of the patient table 2 and the horizontal movement of the roof panel 16 through an interlock according to whether or not the roof panel 16 has been delivered and on the basis of the result of comparison between the height of the patient table 2 and the height HG of the lower end of the aperture 1a of the scanner gantry 1.

That is, the detector 24 in FIG. 3 is transmitting an ultrasonic wave to judge whether or not the roof panel 16 in FIG. 3 has been delivered (Step ST0).

If it is detected by the detector 24 that the roof panel 16 has been delivered (Step ST1), when the height H of the patient table 2 in FIG. 3 is higher than the height HG of the aperture 1a of the scanner gantry 1 (Step ST 2), the patient table 2 can be moved only upwardly (Step ST3), and the roof panel 16 can be moved horizontally in the IN/OUT direction (Step ST4).

On the other hand, when the height H of the patient table 2 is lower than the height HG of the aperture 1a of the scanner gantry 1 (Step ST5), the patient table 2 can be moved both upwardly and downwardly (Step ST6), and the roof panel 16 can be moved horizontally only in the OUT direction (Step ST7).

On the other hand, if it is detected by the detector 24 that the roof panel 16 has not yet been delivered (Step ST8), when the height H of the patient table 2 is higher than the height HG of the aperture 1a of the scanner gantry 1 (Step ST9), the patient table 2 can be moved both upwardly and downwardly (Step ST10), and the roof panel 16 can be moved horizontally in the IN/OUT direction (Step ST11).

On the other hand, when the height H of the patient table 2 is lower than the height HG of the aperture 1a of the scanner gantry 1 (Step ST12), the patient table 2 can be moved both upwardly and downwardly (Step ST13), and the roof panel 16 can be moved horizontally in the IN/OUT direction (Step ST14).

In the illustrated embodiment of the present invention, the scanner in which the X-ray tube 7 and the X-ray detector 8, which are disposed to face each other as shown in FIG. 1, are rotated, is called the scanner gantry 1, together with the peripheral mechanisms thereof. In addition, the roof panel 16, which is the object of detection, is capable of rising and lowering on the patient table 2 and also capable of moving horizontally.

The roof panel 16 of the patient table 2 is moved into the opening 1a (also know as aperture), which is provided in the scanner gantry 1, and set in position. Thereafter, diagnostic data is collected by X-ray exposure.

The embodiment of the present invention particularly has the following features:

The ultrasonic detector 24 is installed in the gap between the scanner gantry 1 and the patient table 2.

When the roof panel 16 is delivered from the patient table 2, the ultrasonic detector 24 detects the projection of the roof panel 16 to confirm the delivery of the roof panel 16 and also measures the distance D from it to the roof panel 16.

The scanner gantry control computer 11 predicts an interference between the roof panel 16 and the scanner gantry 1 and decides whether or not to allow the movement of the roof panel 16 and the patient table 2.

As has been described above, the embodiment of the present invention enables prevention of an interference between the roof panel of the patient table and the scanner gantry simply by detecting the delivery (projection) of the roof panel toward the scanner gantry without directory measuring the absolute position of the roof panel. Thus, the safety in operation can be improved.

In addition, since it is possible to decide whether or not the roof panel is present in the X-ray photographing region, it is possible to prevent a failure in offset measurement. Thus, it is possible to improve both the image quality and the operating efficiency.

Since it is particularly preferable for the detector to use an ultrasonic wave, the detector can also be used as a sensor for measuring a change in distance in the same way as in the case of a potentiometer.

Since an ultrasonic wave is used for detection, various merits are provided. That is, the delivery (or projection) of the roof panel and the distance can be measured independently of the material of the roof panel. Moreover, there is no advantage effect on the human body.

Incidentally, the present invention is not limited to the foregoing embodiment.

For example, the present invention can be applied to not only X-ray CT systems but also medical inspection systems of other types or in other fields, which have a medical inspection part and a patient table, e.g., emission CT systems (nuclear medical diagnostic systems) such as MRI (Magnetic Resonance Imaging) system, magnetic resonance SPECT (Single Photon Emission CT), PET (Position Emission CT), etc.

As has been described above, according to the present invention it is possible to prevent an interference between the medical inspection part and the patient table simply by detecting the delivery (projection) of the roof panel of the patient table without directly measuring the absolute position of the roof panel. Thus, safety can improved.

In addition, since it is possible to decide whether or not the patient table interferes with the medical inspection part, when the present invention is applied to an X-ray CT system, for example, it is possible to prevent a failure in offset measurement and hence possible to improve the image quality and the operating efficiency.

What is claimed is:

1. A medical inspection system comprising:
   a medical inspection apparatus for medical inspection of a patient, said inspection apparatus including a gantry;
   a patient table for supporting the patient thereon and for moving the patient into said medical inspection apparatus gantry; and
   a position detector for detecting the movement of said patient table toward said medical inspection apparatus gantry and for issuing a signal indicative of a predetermined portion of said patient table being at a predetermined position located outside of said medical inspection apparatus gantry, and wherein said position sensor senses the height of the patient table.

2. A medial inspection system according to claim 1, wherein said medial inspection apparatus is an X-ray CT inspection apparatus.

3. A medial inspection system according to claim 1, wherein said position detector is disposed outside of said medical inspection apparatus and at a level which is lower than said patient table.

4. A medial inspection system according to claim 1, wherein said position detector detects the movement of said patient table by using an ultrasonic wave.

5. A medial inspection system according to claim 1, wherein said position detector is connected to a control circuit which generates a signal through an output circuit when a roof panel of said patient table approaches to within a predetermined distance of said medial inspection apparatus gantry.

6. A method of locating a movable patient table for placing a patient thereon in a medical inspection system, said method comprising the steps of:
   sensing the position of the patient table while it is completely outside of a medical inspection apparatus of the medical inspection system; and
   preventing movement of said table toward said medical inspection apparatus in the event that said position sensing step indicates that interference between said patient table and said medical inspection apparatus will occur.

7. A method according to claim 6, wherein the movement of said patient table is detected using a height detector which uses an ultrasonic wave.

8. A method according to claim 6, wherein the medical inspection apparatus includes a scanner gantry of an X-ray CT system.

9. A medical inspection system according to claim 1, wherein said medical inspection apparatus gantry is pivotal about a horizontal axis, and which further comprises a control circuit which is responsive to said position sensor and to a gantry tilt angle.

10. A medical examination apparatus comprising:
    a non-invasive examination unit for radiological examination of a patient;
    a patient table;
    means for moving said patient table both vertically and horizontally with respect to the non-invasive examination unit;
    a single ultrasonic sensor for sensing both a height of the patient table and a horizontal displacement of said patient table wherein interference between said patient table and said non-invasive examination unit can occur.

11. A medical examination apparatus according to claim 10, wherein said non-invasive examination unit includes a gantry which is pivotal about a horizontal axis.

12. A medical examination apparatus according to claim 11, further comprising a control circuit which is responsive to the output of said sensor and to an angle at which said gantry is pivoted about the horizontal axis.

13. A medical examination apparatus according to claim 10, wherein said non-invasive examination unit is a non-invasive radiological medical examination apparatus.

14. A medical inspection system comprising:
    a gantry which forms part of medical inspection apparatus;
    a patient table supported on a floor, said patient table being movable horizontally from a first position outside of said gantry to a second position wherein at least a portion of said patient table is located within said gantry, said patient table being vertically adjustable to vary the height of the table above the floor, said table having a roof panel with a leading edge which extends toward said gantry; and
    a single upwardly oriented ultrasonic position detector supported on the floor at a location outside of said gantry and between said patient table and said gantry for issuing an ultrasonic beam vertically upward along a trajectory which is non-intersective with said gantry, said position sensor producing an output in response to the leading edge of the roof panel intersecting the ultrasonic beam and reflecting the beam back to said position sensor to provide an indication of both lateral and vertical height displacement of the roof panel.

15. A medical inspection system as set forth in claim 14, further comprising control circuit means responsive to said position detector for stopping movement of said table in the event that a collision between said table and said gantry is indicated by the positional relationship between the roof panel and said gantry.

* * * * *